United States Patent [19]

Heuck

[11] 4,185,963
[45] Jan. 29, 1980

[54] METHOD FOR DETERMINING LIPIDS IN BLOOD SERUM

[76] Inventor: Claus-Christian Heuck, Birkenweg 20, 6901 Wilhelmsfeld, Fed. Rep. of Germany, 6901

[21] Appl. No.: 839,091

[22] Filed: Oct. 3, 1977

[51] Int. Cl.² .......................................... G01N 33/16
[52] U.S. Cl. .................................................. 23/230 B
[58] Field of Search ...................................... 23/230 B

[56] References Cited
U.S. PATENT DOCUMENTS 4,039,285  8/1977  Teipel .................................. 23/230 B

OTHER PUBLICATIONS

C. C. Heuck and G. Schlierf, Clinical Chemistry, 23, (3), 536–540, (Mar. 1977).

Primary Examiner—Sidney Marantz
Attorney, Agent, or Firm—Sprung, Felfe, Horn, Lynch & Kramer

[57] ABSTRACT

Lipids in blood serum are directly determined by extracting the pre-$\beta$-lipoprotein (very low density lipoprotein) and chylomicrons and $\alpha$-lipoproteins (high density lipoproteins) from the serum by treatment of the serum with a polycation and optionally wih a weak ion exchanger and/or a strongly polar lipophilic adsorber, and then measuring the lipid content of the $\beta$-lipoproteins in the serum.

14 Claims, 1 Drawing Figure

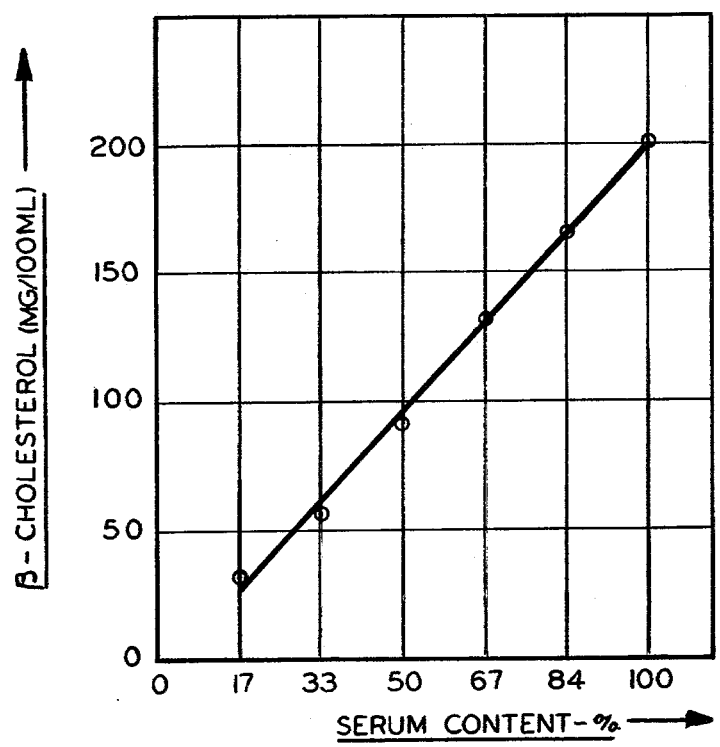

METHOD FOR DETERMINING LIPIDS IN BLOOD SERUM

The invention relates to determining lipids in blood serum.

The determination of the cholesterol and/or triglyceride content in the low density lipoprotrein (LDL) fraction of blood serum is an important laboratory technique for testing in the differential diagnosis of fat metabolism functions. One of the methods used heretofore for the direct determination of the β-cholesterol content was ultracentrifugation in a density gradient.

This prior method utilizes, for the separation of the three lipoprotein components in the serum, namely 1. α-Lipoprotein (high density lipoprotein (HDL), molecule diameter 75–100 Å);
2. β-Lipoprotein (low density lipoprotein (LDL), molecule diameter 150–200 Å); and
3. Pre-β-lipoprotein (very low density lipoprotein (VLDL), molecule diameter 300–700 Å)+-chylomicrons (molecule diameter 1000–10,000 Å), the different specific masses of the three components to be separated, HDL, LDL and VLDL. However, this ultracentrifugation method is very expensive and burdensome. The fractionation must be performed in two operations with high centrifugal forces (105,000 g). The method requires a time expenditure of 8 to 40 hours. Since the ultracentrifuge must in some cases run for 2×20 hours for the complete separation, it is clear that great wear and tear on materials must be anticipated, and thus the method is not suitable as a routine method.

Other conventional separating methods permit no more than indirect determinations. In such methods, the lipoproteins are fractionally precipitated with polyanions and bivalent metal salts (heparin or dextransulfate and calcium chloride, magnesium chloride or manganese chloride). The determination of the β-cholesterol content is in this case accomplished by subtraction of the cholesterol contents from the isolated lipoprotein precipitates.

The combination of ultracentrifugation with polyanion precipitation is used in routine diagnosis. The test time in this case still amounts to 24 hours.

The present invention provides a method for the determination of lipids in blood serum which assures the same results as the conventional methodology using ultracentrifugation, but which avoids the above-mentioned disadvantages.

Essentially, the process of the invention comprises extracting the pre-β-lipoproteins (VLDL) and α-lipoproteins (HDL) from the serum by treatment with a polycation, which can be derived hydrophobically and, if desired, with a weak ion exchanger and/or a strongly polar adsorber having a lipophilic character, and then measuring the lipid content of the β-lipoproteins (LDL) in the serum.

Hydrophobic derivation of the polycation means, that the polycation is substituted by hydrophobic radicals known to a person skilled in the art.

It has been found that especially acyl-substituted or alkyl-substituted polycations or mixtures of same with the unsubstituted polycations are better adsorbents for the extraction of the HDL and VLDL fractions of serum than the unsubstituted polycation alone. The use of these compounds has proven to be especially advantageous because:

1. Relatively smaller amounts suffice. The amount required will be about 1/5 of the unsubstituted polymer.
2. The reagent solution is considerably less viscous than it is when unsubstituted polycation is used.
3. Enzymatic determinations of the lipids can be made in some cases even in the presence of the polycation. Thus an enzymatic method of determination is made possible in addition to a chemical one.

It is advantageous to use polyethyleneimine or acylated or alkylated polyethyleneimine as the polycation, adding it to the serum in amounts totaling from 0.1 to 2 weight-percent final concentration.

The substituents can be especially long-chain fatty acid residues or the corresponding alkyl residues, which can be saturated and/or unsaturated and/or branched, a chain length of the residues of approximately 6 to 26 carbon atoms having proven to be advantageous. A chain length ranging from about 10 to 20 carbon atoms has proven to be especially suitable. The saturated acyl residues, to give a few examples, can be those which are derived from the following acids, the number of the carbon atoms being given between parentheses: capronic ($C_6$), caprylic ($C_8$), pelargonic ($C_9$), capric ($C_{10}$), undecylic ($C_{11}$), lauric or dodecylic ($C_{12}$), tridecylic ($C_{13}$), myristic ($C_{14}$), pentadecylic ($C_{15}$), palmitic ($C_{16}$), margaric ($C_{17}$), stearic ($C_{18}$), nonadecylic ($C_{19}$), arachic ($C_{20}$), behenic ($C_{22}$), lignoceric ($C_{24}$) and cerotinic ($C_{26}$) acid.

Examples of the unsaturated acids are the mono-, di- and tri-unsaturated $C_{18}$ acids, such as oleic acid (cis-$\Delta^9$-dehydrostearic acid), linolic acid (cis.cis-$\Delta^{9,12}$-dehydrostearic acid and linolenic acid (all-cis-$\Delta^{9,12,15}$-dehydrostearic acid). Isovalerianic acid is an example of a branched fatty acid.

The degree of substitution of the primary and secondary amino groups advantageously amounts to from about 35 to 40% in the case of the shorter chain length of the residues to about 5 to 10% in the case of the longer-chain residues.

Cation exchangers having weakly acid, polar functional groups, such as carboxyl groups, have proven to be suitable ion exchangers, such as Amberlite IRC 50. The use of cation exchangers on a methacrylic acid-divinylbenzene basis has produced very well repeatable results. Good highly polar adsorbers of a lipophilic character have proven to be nitrosated polymers on a polystyrene basis, that is, containing aminoxide groups, such as for example Amberlite XAD-2, particle size 100–200μ (e.g., from Serva, Heidelberg).

It has been found in the case of sera in which the triglyceride content exceeds 1000 mg/100 ml (Type IV and Type V hyperlipidemia) that, after treatment with acylated polymer, treatment with the ion exchanger or with the adsorber of lipophilic character can be dispensed with. The upper, creamy phase is in this case removed, and the lipid is determined in the clear, infranatant phase.

The invention is illustrated by the following examples:

Obtaining of Serum Specimens and Methods of Analysis

Use was made of serum specimens obtained from healthy persons with normolipidemia and from untreated persons with Type IIa, IIb, IV and V hyperlipidemias (Fredrickson's classification), after fasting for one night. The analyses were performed within 12 hours.

Preparation of Acylated Polyethyleneimine

An aqueous solution of polyethyleneimine (Polymin P, BASF AG, Ludwigshafen) is lyophilized for 72 hours to remove the solvent. 1 g of residue is dissolved in 50 ml of methanol (99.6% pure) and 1 g of dodecoyl chloride (Fluka, Ulm) is added dropwise to this solution at 25° C. with stirring. The mixture is stirred for 24 hours at 50° C. Then 100 ml of benzene (p.a., Merck, Darmstadt) is added and the solution is concentrated by evaporation in vacuo to such an extent that the acylated polymer precipitates. The precipitate is washed thrice with 100 ml of benzene to remove the free dodecanic acid and unreacted dodecoyl chloride. It is concentrated by evaporation to the dry state and the residual dodecoyl polyethyleneimine is dissolved in distilled water such that a 5% solution results.

In like manner, the linolyl polyethyleneimine is prepared.

Preparation of Alkylated Polyethyleneimine

This is performed in accordance with I. S. Scarpa, H. C. Kiefer and I. M. Klotz, Intrascience, Chem. Rept. 8, Nos. 1–3, 1974, pp. 45 sqq.

Determination of the LDL Lipids 1. 1.5 ml of human serum is shaken in a glass reaction vessel with 50 µl of a 40% polyethyleneimine solution (Polymin P, BASF, Ludwigshafen, German Federal Republic) at 20° C. for 15 minutes. 0.4 g of a weakly acid cation exchanger in form H, e.g., a methacrylic acid-divinyl benzene copolymer (IRC-50 P.A., Serva, Heidelberg, German Federal Republic) is added in granule form and the mixture is shaken for 10 minutes. After another ten minutes the supernatant is decanted and the determinations specified below are performed on this solution.

2. 40 µl of a 5% aqueous solution of dodecoyl polyethylene imine is mixed with 1.4 ml of human serum. The mixture is shaken for 5 minutes by hand or centrifuged (60 rpm). Then 0.4 g of Amberlite IRC 50 granules (Serva, Heidelberg) is added and the mixture is centrifuged for ten minutes at low speed and then for two minutes at 2000 to 3000 rpm, so that a clear supernatant is obtained. This is used for the cholesterol and triglyceride determination.

The cholesterol is determined chemically by the methods of Zack and Liebermann-Burchard, or enzymatically. The found cholesterol content corresponds to the $\beta$-cholesterol content in the serum. The triglyceride determination is performed by the method of Kessler and Lederer. The triglyceride content is given by the difference between the blank value from the total serum (=content of free glycerin in the serum) and the value measured from the above-described supernatant. Cholesterol and triglycerides can also be determined all automatically in a conventional manner, e.g., in the Technicon AA II apparatus, from isopropanol extracts after treatment with zeolite.

3. For comparison, cholesterol and triglycerides are determined after fractionation of the lipoproteins in the serum in the following manner:

3 ml of human serum is centrifuged at 105,000 g for 20 hours with a 40.3 rotor in a Beckmann centrifuge in a discontinuous density gradient with the density 1.006. The VLDL lipoproteins are in the solution having the density of less than 1.006, and the LDL and HDL lipoproteins are in the solution with the density greater than 1.006. The LD lipoproteins are separated from the HD lipoproteins by precipitation with heparin and manganese chloride. The cholesterol is measured by the Zack or Liebermann-Burchard method from the fraction which contains the HDL and LDL, and from the fraction which contains the HDL. The $\beta$-cholesterol is calculated from the difference between the cholesterol content of the HDL and LDL fraction and that of the HDL fraction. The recovery calculation in the ultracentrifugation method is performed by adding the VLDL and the LDL/HDL values. It is compared with the cholesterol content in the whole serum.

Results

1. Tests with polyethyleneimine

In Table 1 a number of experimental values are compared with values measured by the ultracentrifugal method.

A comparison of the $\beta$-cholesterol determination by means of ultracentrifugation with extraction with polyethyleneimine and the cation exchanger on 100 human serums shows a correlation of 95% $K_k = 0.95$. Over a range from 50 mg% to 500 mg% of $\beta$-cholesterol, the correlation curve is linear with a function:

$$Y_{Extr.} = 1.06 \cdot X_{UC} - 5.02$$

As the function of the straight lines shows, in the extraction method a $\beta$-cholesterol value is determined which, in comparison to determination by ultracentrifugation, is 5 mg higher. This difference can be attributed to a loss of cholesterol in the separation by means of ultracentrifugation, which amounts to a maximum of up to 15%.

The study of a dilution series in serums whose lipoprotein content has been modified by the addition of a 6% albumin solution showed a linear decrease of the $\beta$-cholesterol content after extraction with polyethylene imine and the cation exchanger (FIG. 1).

The repeatability of the $\beta$-cholesterol determination from aliquot volumes of the same serum which have been treated in the same manner with polyethyleneimine and the cation exchanger is more precise (variation coefficient $v_k$: 2.4) than that of ultracentrifugation (variation coefficient $v_k$: 5.9) (Table 2).

The serums of one patient, which were tested by both methods in a control series of several weeks, showed an agreement among the $\beta$-cholesterol determinations which is entirely adequate for clinical purposes (Table 3).

The testing of serums having an extremely high content of triglycerides (Type IV, Type V) or an extremely high content of cholesterol (Type II) by extraction with polyethyleneimine and the cation exchanger yielded $\beta$-cholesterol values which have to be evaluated in the same manner as the determination made by ultracentrifugation (Table 4).

Table 1

Comparison of $\beta$-cholesterol determination by means of:
1. the polyethyleneimine extraction method
2. the ultracentrifugation-precipitation method.

| Total cholesterol | $\beta$-cholesterol (extraction method) | $\beta$-cholesterol (UC-precipitation) method |
|---|---|---|
| 144 mg/100 ml | 107 mg/100 ml | 102 mg/100 ml |
| 137 mg/100 ml | 78 mg/100 ml | 81 mg/100 ml |
| 153 mg/100 ml | 86 mg/100 ml | 72 mg/100 ml |
| 155 mg/100 ml | 123 mg/100 ml | 123 mg/100 ml |
| 171 mg/100 ml | 121 mg/100 ml | 120 mg/100 ml |
| 164 mg/100 ml | 116 mg/100 ml | 124 mg/100 ml |

Table 1-continued

Comparison of β-cholesterol determination by means of:
1. the polyethyleneimine extraction method
2. the ultracentrifugation-precipitation method.

| Total cholesterol | β-cholesterol (extraction method) | β-cholesterol (UC-precipitation) method |
|---|---|---|
| 224 mg/100 ml | 189 mg/100 ml | 201 mg/100 ml |
| 220 mg/100 ml | 179 mg/100 ml | 185 mg/100 ml |
| 249 mg/100 ml | 199 mg/100 ml | 189 mg/100 ml |
| 250 mg/100 ml | 193 mg/100 ml | 190 mg/100 ml |
| 277 mg/100 ml | 101 mg/100 ml | 106 mg/100 ml |
| 291 mg/100 ml | 241 mg/100 ml | 221 mg/100 ml |
| 326 mg/100 ml | 281 mg/100 ml | 275 mg/100 ml |
| 309 mg/100 ml | 172 mg/100 ml | 164 mg/100 ml |
| 315 mg/100 ml | 252 mg/100 ml | 245 mg/100 ml |
| 352 mg/100 ml | 266 mg/100 ml | 261 mg/100 ml |
| 341 mg/100 ml | 208 mg/100 ml | 224 mg/100 ml |
| 350 mg/100 ml | 139 mg/100 ml | 149 mg/100 ml |
| 383 mg/100 ml | 352 mg/100 ml | 313 mg/100 ml |
| 435 mg/100 ml | 396 mg/100 ml | 373 mg/100 ml |
| 446 mg/100 ml | 388 mg/100 ml | 396 mg/100 ml |
| 446 mg/100 ml | 388 mg/100 ml | 396 mg/100 ml |
| 470 mg/100 ml | 448 mg/100 ml | 418 mg/100 ml |
| 505 mg/100 ml | 483 mg/100 ml | 466 mg/100 ml |

Dilution Series

Content of β-cholesterol in serum after extraction of VLDL and HDL with polyethyleneimine and a DVB-methacrylic acid copolymer cation exchanger after dilution with a 6% human albumin solution.

The values determined are plotted in FIG. 1 which is a plot of β-cholesterol values against serum content.

Table 2

Repeatability of β-cholesterol determination in a serum by:
1. Extraction with polyethyleneimine and IRC 50
2. Polyanion precipitation and ultracentrifugation.
Total value of the serum cholesterol: 509 mg/100 ml

| Determination Number | 1. Extraction method | 2. Ultracentrifugation-precipitation method |
|---|---|---|
| No. 1 | 448 mg/100 ml | 471 mg/100 ml |
| 2 | 426 mg/100 ml | 428 mg/100 ml |
| 3 | 425 mg/100 ml | 457 mg/100 ml |
| 4 | 433 mg/100 ml | 471 mg/100 ml |
| 5 | 437 mg/100 ml | 383 mg/100 ml |
| 6 | 428 mg/100 ml | 435 mg/100 ml |
| 7 | 429 mg/100 ml | 458 mg/100 ml |
| 8 | 436 mg/100 ml | 418 mg/100 ml |
| 9 | 437 mg/100 ml | 426 mg/100 ml |
| 10 | 426 mg/100 ml | 445 mg/100 ml |
| 11 | 433 mg/100 ml | 474 m/100 ml |
| 12 | 412 mg/100 ml | 474 mg/100 ml |
| 13 | 403 mg/100 ml | 455 mg/100 ml |
| 14 | 430 mg/100 ml | 416 mg/100 ml |
| 15 | 430 mg/100 ml | 459 mg/100 ml |
| 16 | 436 mg/100 ml | |
| Average | 429 mg/100 ml | 455 mg/100 ml |
| Standard Deviation | 10.4 mg/100 ml | 26.5 mg/100 ml |
| Variation Coefficient | 2.42 | 5.95 |

Table 3

Continuous control of the β-cholesterol of a person as determined by the extraction method and by the ultracentrifugation-precipitation method over a period of several weeks.

| Total cholesterol in the serum | β-cholesterol by the extraction method | β-cholesterol by the ultracentrifugation-precipitation method |
|---|---|---|
| 266 mg/100 ml | 198 mg/100 ml | 220 mg/100 ml |
| 308 mg/100 ml | 215 mg/100 ml | 233 mg/100 ml |
| 220 mg/100 ml | 166 mg/100 ml | 170 mg/100 ml |
| 244 mg/100 ml | 193 mg/100 ml | 189 mg/100 ml |
| 197 mg/100 ml | 179 mg/100 ml | 185 mg/100 ml |
| 198 mg/100 ml | 128 mg/100 ml | 127 mg/100 ml |
| 201 mg/100 ml | 156 mg/100 ml | 153 mg/100 ml |
| 197 mg/100 ml | 142 mg/100 ml | 160 mg/100 ml |
| 199 mg/100 ml | 144 mg/100 ml | 140 mg/100 ml |
| 219 mg/100 ml | 195 mg/100 ml | 157 mg/100 ml |
| 218 mg/100 ml | 197 mg/100 ml | 169 mg/100 ml |

Table 4

| Type | Total TG | Total Chol. | β-Chol.(UC) | β-Chol.(Extr.) |
|---|---|---|---|---|
| 5 | 1720 | 401 | 87 | 105 |
|   | 1305 | 393 | 64 | 33 |
|   | 1360 | 340 | 65 | 70 |
| 4 | 815 | 277 | 89 | 132 |
|   | 690 | 372 | 109 | 110 |
|   | 820 | 348 | 145 | 135 |
| 2 | 167 | 508 | 464 | 449 |
|   | 239 | 512 | 466 | 483 |
|   | 252 | 497 | 452 | 487 |

2. Tests Performed With Acylated Polyethyleneimine

Table 5a contains a list of various fractionations showing the repeatability of the determination of the triglyceride and cholesterol contents. The concentration of the polycation or polycation mixture and the weight ratios of unsubstituted polycation to acylated polycation are given between parentheses. Table 5b contains 18 repetitive measurements performed using a 2:1 adduct.

Table 5a

List of fractionation preparations and the triglyceride and cholesterol contents determined after fractionation.

PEI = Polyethyleneimine
PEI-C$_{12-0}$ = Dodecoyl-PEI
PEI-C$_{18-2}$ = Linolyl-PEI

| | TG (mg %) | Chol. (mg %) |
|---|---|---|
| Serum Total amount in serum | 121 | 176 |
| | 120 | 177 |
| 1.5 ml + 0.05 ml (20%) PEI + Amberlite IRC 50 | 50 | 157 |
| | 43 | 157 |
| 1.5 ml + 0.05 ml (20%) PEI-C$_{12-0}$ (1:2) + Amberlite IRC 50 | 40 | 128 |
| | 50 | 132 |
| | 41 | 130 |
| 1.5 ml + 0.05 ml (20%) PEI-C$_{12-0}$ (1:1) + Amberlite IRC 50 | 27 | 102 |
| | 32 | 103 |
| | 28 | 99 |
| 1.5 ml + 0.05 ml (40%) PEI-C$_{18-2}$ (1:3.2) + Amberlite IRC 50 | 76 | 114 |
| | 75 | 112 |
| | 81 | 116 |

Table 5b

Repeated measurements performed on one serum
1.4 ml of serum + 0.05 ml (10%) PEI-C$_{12-0}$ (2:1) + IRC 50

| Tg (mg%) | 35 | 37 | 41 | 35 | 35 | 37 | 38 | 36 | 35 |
| Chol. (mg%) | 125 | 127 | 126 | 125 | 125 | 123 | 123 | 127 | 127 |

Table 6

The quantities are given in milligrams per hundred milliliters

| | Total cholesterol | | Total TG | | | | | | | | | |
|---|---|---|---|---|---|---|---|---|---|---|---|---|
| | Whole serum | Recov. (UC) | Whole serum | Recov. (UC) | LDL Chol. (UC) | C.V. | LDL Chol. (extr.) | C.V. | LDL TG (UC) | C.V. | LDL TG (extr.) | C.V. |
| normal (n:19) | 178 | 175 | 111 | 98 | 108 ± 5 | 4.6 | 123 ± 3 | 2.5 | 31 ± 5 | 16.1 | 28 ± 4 | 13 |
| Type IIb (n:16) | 289 | 287 | 211 | 182 | 205 ± 11 | 5.5 | 211 ± 13.5 | 6.4 | 79 ± 5 | 6.3 | 83 ± 6 | 7.7 |
| Type IV (n:19) | 258 | 245 | 299 | 255 | 169 ± 7 | 4.1 | 183 ± 5 | 2.7 | 81 ± 5 | 6.2 | 85 ± 7 | 8.1 |
| Type V (n:16) | 1130 | 689 | 4100 | 1987 | 59 ± 11 | 19 | 132 ± 4 | 3.4 | 63 ± 12 | 19 | 153 ± 8 | 5.1 |

Whole serum = Total cholesterol or total triglycerides in the unfractionated serum
Recov. (UC) = Recovery values after ultracentrifugation (density gradient)
LDL Chol. or TG (UC) = Determined after ultracentrifugation (density gradient) and polyanionic precipitation
LDL Chol. or TG (Extr.) = Determined by the method of the invention.
C.V. = Coefficient of variation
n = number of measurements Repeated measurements performed on one serum
1.4 ml of serum + 0.05 ml (10%) PEI-$C_{12-0}$ (2:1) + IRC 50

| TG (mg%) | 35 | 36 | 40 | 37 | 41 | 37 | 36 | 42 | 37 |
|---|---|---|---|---|---|---|---|---|---|
| Chol. (mg%) | 120 | 118 | 123 | 119 | 123 | 126 | 126 | 119 | 121 |

Total amount in the serum: TG (mg%)  111  103
Chol (mg%)  178  175

In the case of the 1:1 product, a 5% solution has proven to be the optimum.

The corresponding experimental findings obtained with the 5% solution of dodecoylated polyethyleneimine prepared in accordance with the foregoing example are contained in Table 6.

A comparison of the LDL cholesterol determination by ultracentrifugation with the method of the invention, using serum specimens from subjects with normolipidemia and hyperlipidemia shows that the results are good both in the case of lower triglyceride concentration (normal and Type IIa lipidemia; correlation coefficient r=0.94) and in the case of triglyceride-rich specimens (Type IV and Type IIb, r=0.95). For triglycerides the correlation (r=0.80) is not quite as good as it is for cholesterol.

The precision of the LDL cholesterol and LDL triglyceride determination was tested by the use of serum specimens obtained from subjects with normolipidemia and Type IIb, Type IV and Type V hyperlipidemia (Table 6). These determinations were obtained after fractionation with a 5% solution of dodecoylated polyethyleneimine and Amberlite IRC 50 as set forth in the foregoing example. The variation coefficient is between 2.5 and 6.4 for cholesterol and 5.1 to 13.0 for triglycerides (Table 6). It is to be stated in explanation of Table 6 that, in the case of Type V, values are obtained in the fractionation of the invention which are about twice as high as in the case of ultracentrifugation. In these serum specimens, only 60% of the cholesterol and 48% of the triglycerides is recovered by means of density gradient centrifugation.

The present findings show that the method of the invention offers an outstanding technical advance over the ultracentrifugation method, particularly due to the considerably reduced expenditure of time, material and labor, and in comparison with the ultracentrifugation method combined with polyanionic precipitation it additionally offers improved precision. Since particularly in the case of the hydrophobically derived polycations it is possible to operate with relatively lesser amounts and the solutions have a lesser viscosity, surprisingly even the enzymatic reactions can be performed in the presence of the polycation.

It will be understood that the specification and examples are illustrative but not limitative of the present invention and that other embodiments within the spirit and scope of the invention will suggest themselves to those skilled in the art.

What is claimed is:

1. Method for the direct determination of lipids in blood serum, which comprises extracting the pre-β-lipoprotein (very low density lipoprotein) and chylomicrons and α-lipoproteins (high density lipoproteins) from the serum by treatment of the serum with a polycation, and then measuring the lipid content of the β-lipoproteins (low density lipoproteins) in the serum.

2. Method as claimed in claim 1 wherein said polycation is derived hydrophobically.

3. Method as claimed in claim 1 wherein said treatment is carried out with a weak ion exchanger in addition to said polycation.

4. Method as claimed in claim 1 wherein said treatment is carried out with a strongly polar adsorber having a lipophilic character in addition to said polycation.

5. Method as claimed in claim 1 wherein said treatment is carried out with a weak ion exchanger and a strongly polar lipophilic adsorber in conjunction with said polycation.

6. Method as claimed in claim 1 wherein the polycation is polyethyleneimine.

7. Method as claimed in claim 1 wherein said polycation is an acylated or alkylated polycation.

8. Method as claimed in claim 7 wherein the acyl or alkyl groups of said polycation contain from 6 to 26 carbon atoms.

9. Method as claimed in claim 8 wherein the acyl or alkyl groups of said polycation contain from 10 to 20 carbon atoms.

10. Method as claimed in claim 1 wherein said polycation is used in an amount of from 0.1 to 2 weight percent of the total treated serum composition.

11. Method as claimed in claim 2 wherein said cation exchanger contains carboxyl groups.

12. Method as claimed in claim 2 wherein said cation exchanger is comprised of methacrylic acid and divinylbenzene.

13. Method as claimed in claim 3 wherein said polar lipophilic adsorber is an aminoxide group containing polymer based on polystyrene.

14. Method as claimed in claim 1 wherein said lipids to be determined are selected from the group consisting of cholesterol and triglycerides.

* * * * *